United States Patent [19]
Webinger

[11] Patent Number: 6,009,998
[45] Date of Patent: Jan. 4, 2000

[54] CARDBOARD PACKAGE FOR HOLDING CATHETERS

[75] Inventor: George Paul Webinger, Golden Valley, Minn.

[73] Assignee: Flour City Packaging Corporation, Minneapolis, Minn.

[21] Appl. No.: 09/072,816

[22] Filed: May 5, 1998

Related U.S. Application Data

[60] Provisional application No. 60/046,840, May 5, 1997.

[51] Int. Cl.[7] .................................................. B65D 85/08
[52] U.S. Cl. ........................ 206/364; 206/482; 206/592
[58] Field of Search ..................................... 206/364, 349, 206/305, 306, 477, 478, 480, 482, 592, 443, 587; 200/363

[56] References Cited

U.S. PATENT DOCUMENTS

| | | |
|---|---|---|
| 3,967,728 | 7/1976 | Gordon et al. ........................... 206/364 |
| 4,379,506 | 4/1983 | Davidson ................................. 206/364 |
| 4,923,061 | 5/1990 | Trombley, III .......................... 206/364 |
| 5,105,942 | 4/1992 | Van Veen et al. ....................... 206/364 |
| 5,131,537 | 7/1992 | Gonzales ................................. 206/364 |
| 5,165,540 | 11/1992 | Forney ..................................... 206/364 |
| 5,501,341 | 3/1996 | Van Es ..................................... 206/364 |

*Primary Examiner*—Paul T. Sewell
*Assistant Examiner*—J. Mohandesi
*Attorney, Agent, or Firm*—Merchant & Gould P.C.

[57] ABSTRACT

A catheter holder for holding and retaining a catheter during storage, shipping, and prior to use. The holder includes a base, a plurality of retainers having extendible retaining members, and a channel into which the catheter or a portion of the catheter is inserted. In specific implementations, the holder further comprises openings on the underside of the retainers for opening and extending the extendible retaining members.

13 Claims, 4 Drawing Sheets

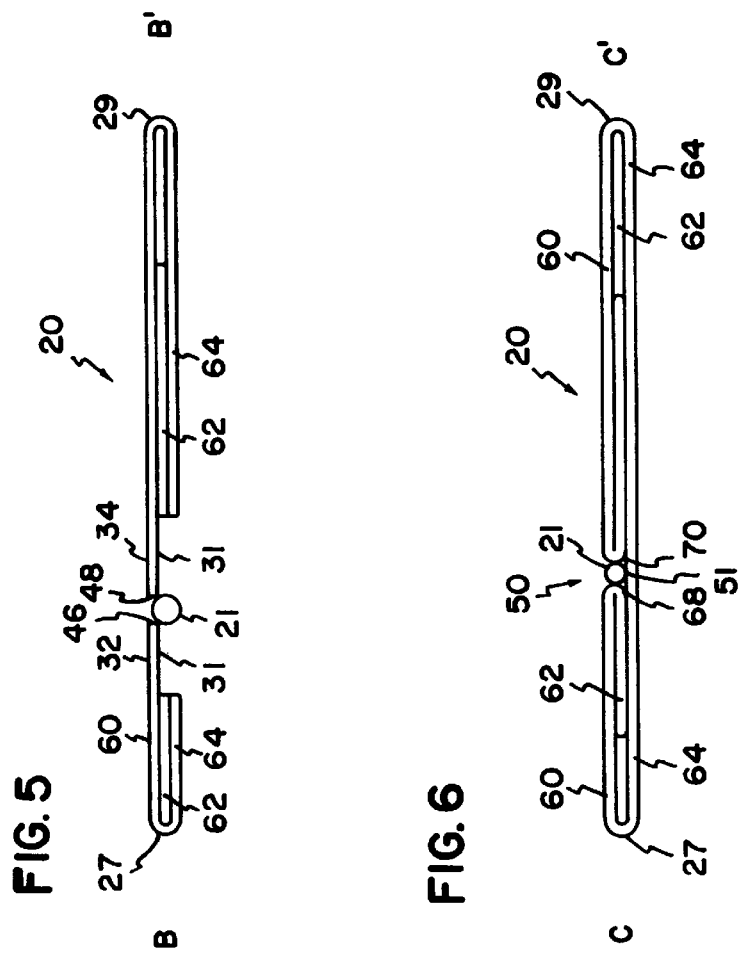
FIG. 5
FIG. 6
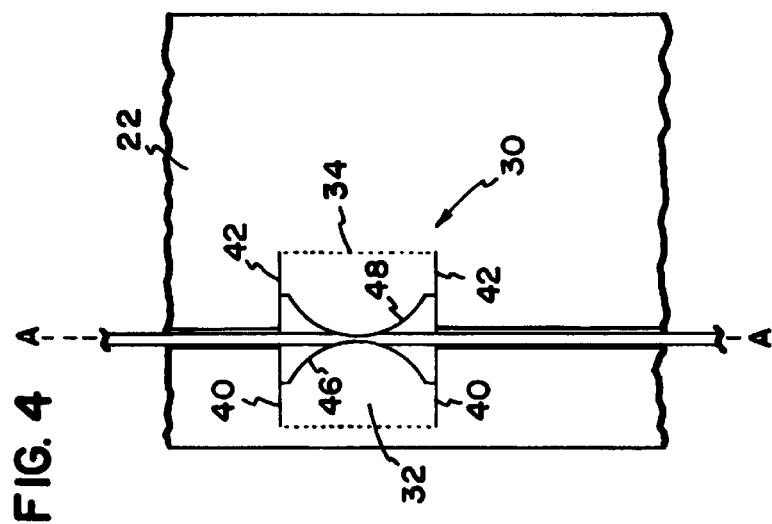
FIG. 4

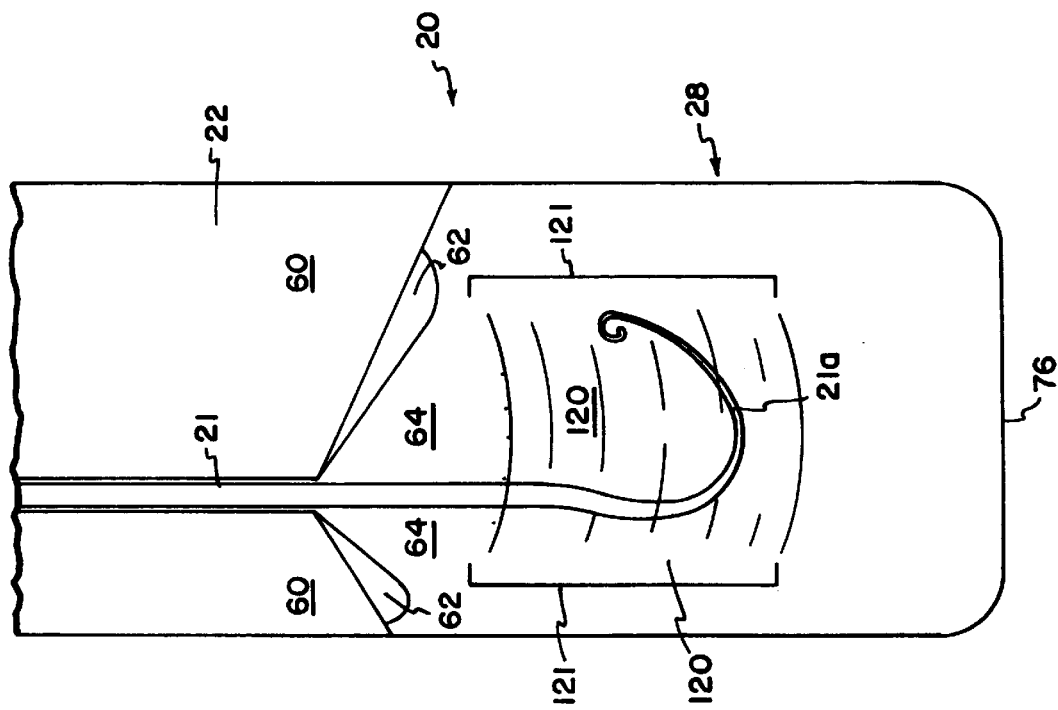
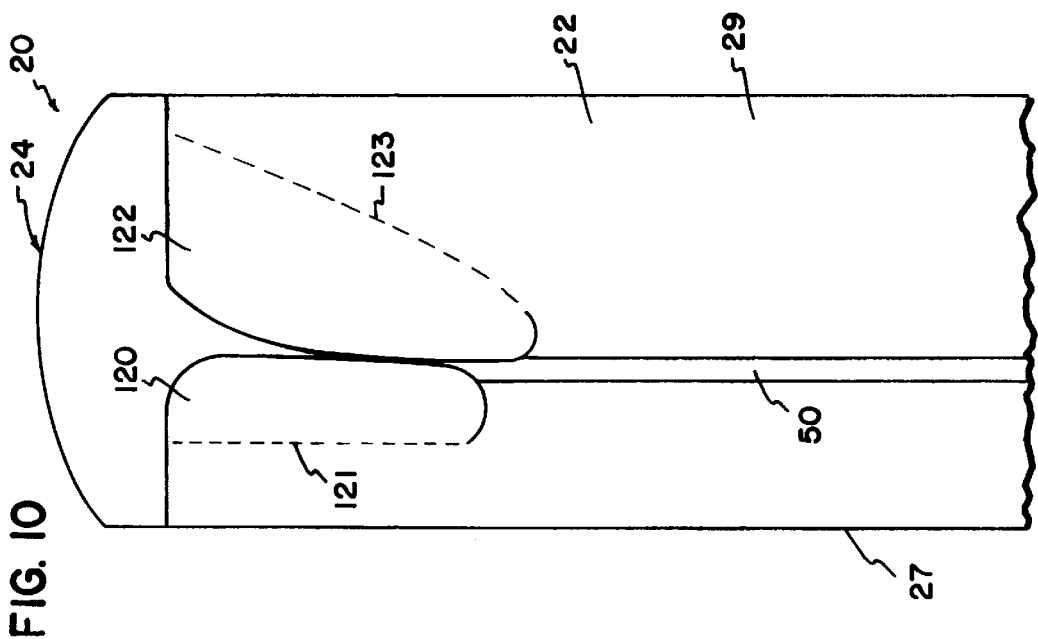

CARDBOARD PACKAGE FOR HOLDING CATHETERS

This application claims benefit of Provisional Application 60/046,840, filed May 5, 1997.

FIELD OF THE INVENTION

The present invention is directed to a holder for retaining a catheter. More specifically, the invention is directed to a card for retaining a catheter within a package, the card is useful for securing the catheter during shipping, storage, and prior to use on a patient.

BACKGROUND OF THE INVENTION

Catheters are tubular medical devices for insertion into canals, vessels, passageways, or body cavities; often to permit the injection or withdrawal of fluid or to keep a passage open. While catheters vary in size, shape, and function, they frequently consist of a very long, flexible, and thin tubular portion connected to a wider, ridged head portion. The tubular portion may be a meter or longer in length, and only a fraction of an inch in diameter. The head may be, for example, an inch or two in length and a half inch in diameter.

The tubular portion of the catheter is usually hollow, and may have one or more lumens running along its entire length. The lumen or lumens function as a way of inserting various devices into the catheter. For example, catheters frequently travel along a guidewire running through one of the lumens. Alternatively, the lumens may receive mechanical devices and control wires for removing clots within blood vessels, for assisting in surgical operations, for retrieving tissue samples, etc.

Due to the extremely fine and often delicate nature of the lumens, as well as the slight tolerances associated with many of the applications to which catheters are applied, catheters must necessarily be handled, stored, and shipped with great care. Mechanical or chemical abrasion to any portion of the exterior of the catheter can cause problems to the subsequent use of the catheter. Also, deformation of the catheter can be a problem if it results in leaving the catheter damaged or transformed in any way. Thus, significant bending of the catheter should normally be avoided during the storage of a catheter to avoid any "memory" of the bends or any pinched lumens. Such binding should also be avoided while installing or removing a catheter from a storage or shipping packaging.

In addition to having a head portion and a tubular portion, many catheters have sophisticated tail ends opposite the head portion. These ends may contain, for example, balloons for use in angeoplasty operations. Thus, it is also necessary that the end of a catheter holder accommodate the tail end of a catheter.

Prior art catheter holders include formed plastic trays having a groove for retaining a catheter, along with a series of rigid tabs designed to hold the catheter within the groove. However, such designs are problematic in that the catheter must often be somewhat deformed or bent in order to be implaced behind the tabs. Since the tabs are substantially rigid in nature, they do not flex out of the way of the catheter and do not provide significant downward force to retain the catheter in place. It is also often true that the groove is configured to retain only a specific size catheter tube. Thus, only a specific diameter will adequately fit within, and be retained by, the groove.

Another type of catheter holder that has been used in the past is constructed from thin cardboard and includes tabs that are cut into the cardboard and retain the catheter. However, this design also requires that the catheter be slightly deformed since the tabs are not lined up with one another. This prior art holder also lacks significant rigidity in the base, and does not contain any additional support for the tube other than the series of cut tabs. Such catheter holders can result in undesirable sliding or other movement of the catheter during shipping.

Thus, a need exists for an improved catheter holder that securely retains a catheter during storage, shipping, and prior to use in a patient.

SUMMARY OF THE INVENTION

The present invention is directed to a holder for retaining a catheter. The holder includes an elongate base member that has a first end, a second end, a top surface, and a bottom surface. At least two retainers are configured and arranged to retain the catheter in place. Each retainer has at least one extendible member for retaining the catheter. The holder also includes a channel in the top surface of the elongate base. This channel connects the retainers to one another along a line, and is also configured to receive the catheter.

In a specific implementation of the present invention, the retainers further include openings in the elongate base member extending from the top surface to the bottom surface of the base member. The openings are configured and arranged to provide access to the extendible member. In other embodiments, said openings are not present.

In certain embodiments of the present invention, each retainer has two extendible members. The extendible members are positioned on opposed sides of the channel. In other embodiments, the extendible members comprise portions of the top surface that extend over the line formed by the channel. More than one retainer is used in most embodiments of the present invention. The number of retainers may be very high in number, but is preferably from two (2) to twenty (20) in number.

The extendible members are positioned substantially opposite from one another in specific implementations of the present invention. In other implementations, the extendible members are positioned substantially across from one another and are partially offset with respect' to one another.

While the elongate base of the present invention may be constructed of numerous different types of materials, in at least one embodiment of the invention the elongate base is constructed of a cellulose-fiber based material. The channel within the base may be constructed by embossing the top surface of the elongate base, by folding the base to form a channel, or by folding and embossing the elongate base.

The elongate base member comprises a first edge and a second edge. The channel is formed in specific implementations by folding the base member such that the first edge and second edge are proximate with one another, and a space between the first and second edges defines the channel.

The above summary of the present invention is not intended to describe each discussed embodiment of the present invention. This is the purpose of the figures and the detailed description which follow.

BRIEF DESCRIPTION OF THE DRAWINGS

FIG. 4 is a top plan view of the catheter holder shown in FIGS. 1, 2 and 3, showing the a tubular portion of a catheter retained by two extendible members of a retainer.

FIG. 5 is a cross sectional view of the catheter holder shown in FIG. 2, the cross section taken along lines B-B$^1$ of FIG. 2.

FIG. 6 is a cross sectional view of the catheter holder shown in FIG. 2, the cross section taken along lines C-C$^1$ of FIG. 2.

FIG. 10 is a top plan view of a tail end of a catheter holder constructed in accordance with an additional embodiment of the present invention for retaining an end of a catheter.

FIG. 11 is a top plan view of a tail end of a catheter holder constructed in accordance with the present invention.

While the invention is susceptible to various modifications and alternative forms, specifics thereof have been shown by way of example and drawings, and will be described in detail. It should be understood, however, that the intention is not to limit the invention to particular embodiments described. On the contrary, the intention is to cover modifications, equivalents, and alternatives falling within the spirit and scope of the invention as defined by the appended claims.

DETAILED DESCRIPTION OF THE INVENTION

The present invention is directed to a holder suitable for retaining a catheter during storage, shipping, and prior to use. The holder includes an elongate base portion with at least two retainers configured to hold the catheter. In certain embodiments of the present invention, the holder further includes a channel connecting the retainers to one another along a line configured to receive the catheter.

Figure 1:
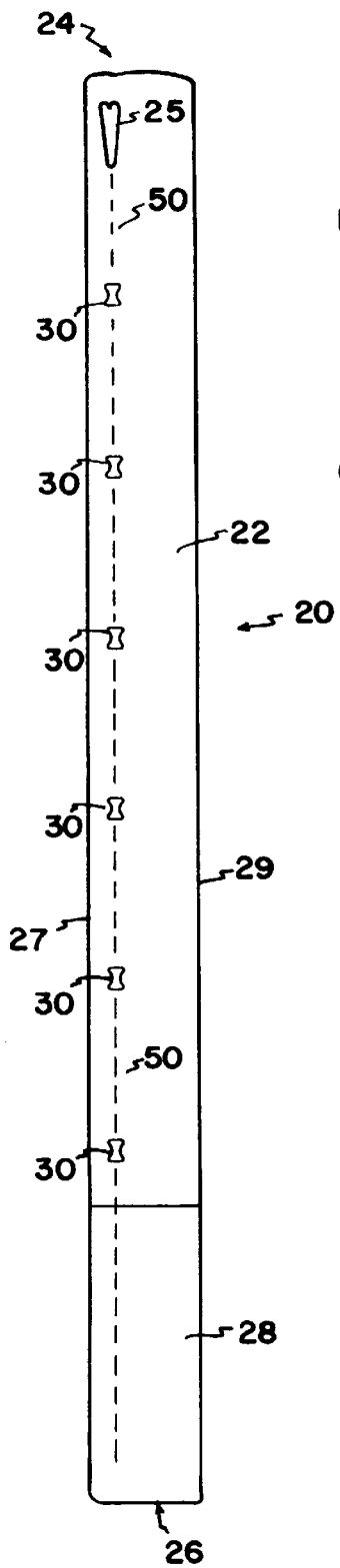
FIG. 1 is a top plan view of a catheter holder constructed in accordance with the present invention, showing a plurality of retainers and a channel for securing a catheter.

Referring now to the Figures, in which like numerals identify like features in the drawings, FIG. 1 is a top plan view of a catheter holder, denoted generally as 20, constructed in accordance with the present invention. Catheter holder 20 shows a number of retainers 30 and a channel 50 running between, and through, the retainers 30. The holder 20 includes a base 22, a head end 24, and a tail end 26. The portion of the base 22 closest to the tail end 26 is identified as the tail portion 28 of the base 22. Edges 27, 29 of the base 22 further define the shape and perimeter of the catheter holder 20.

The holder 20 shown in FIG. 1 includes a head end fastener 25 into which the rigid head of a catheter is inserted and retained (not shown in FIG. 1). The remaining tube of the catheter is placed within the channel 50 running between the retainers 30 and the head end fastener 25.

Figure 2:
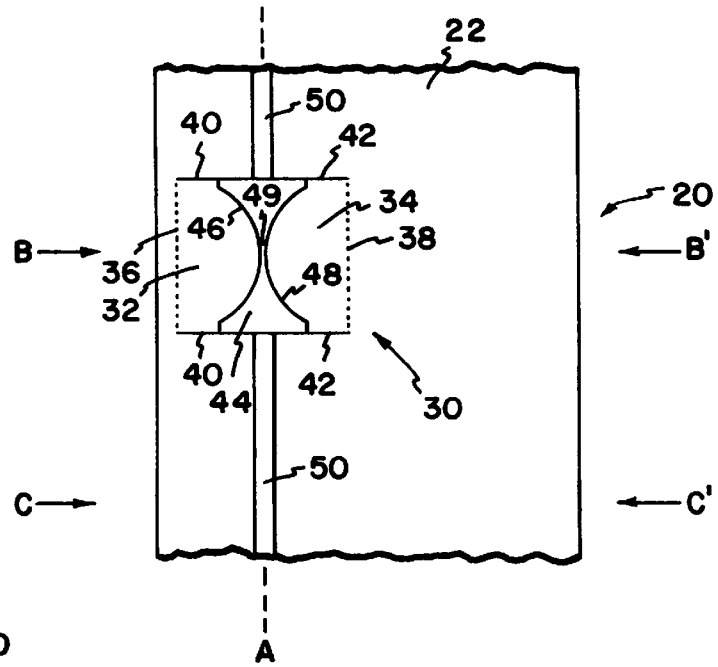
FIG. 2 is a fragmentary top plan view of the catheter holder shown in FIG. 1, showing a retainer having two extendible members in a closed position.
Figure 3:
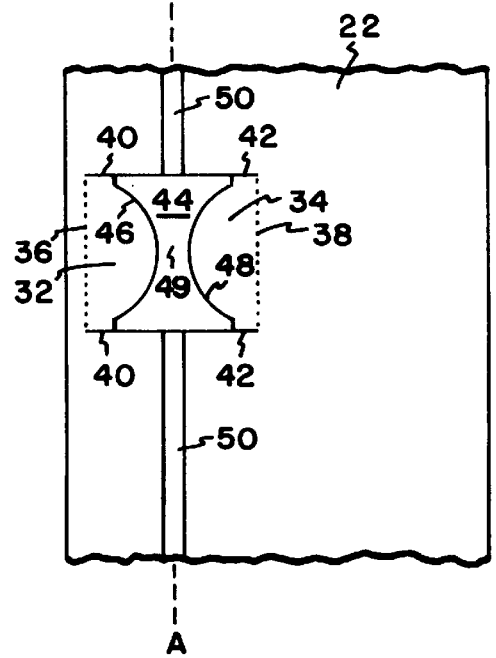
FIG. 3 is a top plan view of catheter holder shown in FIGS. 1 and 2, showing the retainer with two extendible members in an open position.

Referring now to FIGS. 2, 3, and 4, a fragmentary top plan view of the catheter holder shown is FIG. 1 is depicted. Retainer 30 is shown in greater detail, and the two extendible members 32, 34 of the retainer 30 are identified. The extendible members 32, 34 are shown substantially opposite one another and equally spaced from the axis line A-A$^1$ formed by the channel 50. As is readily apparent from FIG. 2, the channel 50 continues on both sides of the retainer 30: a first portion extends above the retainer toward the top end of the catheter holder 20 and a second end extends towards the tail end of the catheter holder 20.

Extendible members 32, 34 include leading edges 46, 48 and pivot lines 36, 38. The extendible members 32, 34 are constructed such that they may substantially pivot along lines 36, 38. In specific embodiments of the present invention, the pivot lines 36, 38 are formed by embossing the base 22. In other embodiments of the present invention, the pivot lines 36, 38 are formed by perforating the base 22, or by perforating and embossing the base 22. In yet other embodiments of the present invention, the pivot lines 36, 38 are not expressly formed by perforation or pivoting, but rather the extendible members 32, 34 pivot naturally when a force is applied to the members 32, 34 proximate the leading edges 46, 48.

In the embodiment shown in FIGS. 2, 3, and 4, the extendible members 32, 34 of the retainer 30 include cut lines 40, 42 extending along the outer edges of the retainer 30. Cut lines 40, 42 permit the extendible members 32, 34 to pivot without folding. The longer the cut line 40, 42, the lower the force necessary to lift the extendible members 32, 34 from the plane formed by the base 22 of the retainer 30.

In the embodiment depicted, an opening 44 is made within the base 22 of the holder 20. Opening 44 is visible in FIG. 2 as a generally "hourglass" shaped form with a narrow center and wide top and bottom. However, as is evident from subsequent FIGS. 3 through 5, opening 44 continues beneath either a portion of the extendible members 32, 34 or the entire extendible members 32, 34.

In other implementations of the present invention, opening 44 is not present, but instead the area below the extendible members 32, 34 is enclosed and solid.

As shown in FIG. 2, a gap 49 exists between the leading edges 46, 48 of the extendible members. While the embodiment shown in FIG. 2 shows this gap 49 as very slight, it will be appreciated that the gap may be greater or lesser than that shown in FIG. 2. In specific embodiments, the gap 49 may be approximately as wide as the channel 50. In all embodiments, the gap is less than or equal to the diameter of a catheter intended to be held by the retainer 30. In certain implementations, the leading edges 46, 48 of the extendible members 32, 34 overlap (not shown).

Referring now specifically to FIG. 3, the extendible members 32, 34 have been flexed upward to receive a catheter tube 21 (shown in FIG. 4). Gap 49 is widened to receive the catheter. In specific embodiments of the present invention, gap 49 is widened by bending the base 22 along line A-A$^1$. Since line A-A$^1$ runs through channel 50, and the extendible members 32, 34 of the retainers 30 are on opposite sides of the channel 50, forces pressing down proximate the outside edges, 27, 29 and up on the back side of the channel 50 will cause the gap 49 to expand and permit the addition of the catheter into the channel. The base 22 is made of a resilient material such that it returns to substantially the same shape it had prior to being bent along axis A-A$^1$. In returning to the earlier shape, the extendible members 32, 34 press down upon and securely hold the catheter 21.

The extendible members flex generally along the pivot lines 36, 38. In certain embodiments, the extendible members 32, 34 are flexed upward by application of an external force. The external force is applied, for example, by pressing from the underside 31 of the retainer (shown in FIG. 5). The pressure applied to the underside may be from a mechanical device that presses on all extendible members 32, 34 of all of the retainers 30 at one time, or may alternatively selectively press on the extendible members 32, 34. Once the force applied to the underside 31 of the extendible members 32, 34 is removed, the flexible members return generally to their original position within the general plane formed by the base 22.

When a catheter tube 21 is within the channel and the retainers, the return of the extendible members to their original position imparts a downward force to the catheter 21 and helps in retaining the catheter 21 within the holder 20. In certain circumstances, the catheter 21 is wide enough that the extendible members 32, 34 do not return to the plane of the base 22, but still apply a force to retain the catheter 21 within the channel 50 of the holder 20.

In FIGS. 2, 3, and 4, the leading edges 46, 48 are shown with a generally arc-shaped outline. It will be appreciated that numerous other shapes for the leading edges 46, 48 are within the scope of the present invention. For example, the leading edges may be straight or rectangular. Also the leading edges may fully conceal the opening 44 beneath them. Furthermore, while the depicted leading edges 46, 48 are mirror images of one another, it will be appreciated that the leading edges may have more than one shape and need not be identical or mirror images.

As will be apparent from FIG. 4, a distance 56 exists between the point 52 where the catheter 21 comes in contact with the base 22 and the point 54 where the catheter 21 comes in contact with the extendible members 32, 34. This distance 56 eliminates "pinch points" or "scissors points" at which the catheter 21 may be faced with opposing pressure causing deformation of the catheter and possible chinking or knotching of the catheter. This distance 56 varies in the different embodiments, but is preferably from 0.05 to 1.0 inch; and more preferably from 0.1 to 0.5 inch. As shown in FIG. 4, the design of the present invention applies a force from the bottom at point 52 and from the top at point 52, thereby avoiding application of the force at substantially adjacent and opposite positions on the catheter 21 tube, thus reducing the likelihood of damage to the catheter 21.

Referring now to FIG. 5, a cross-sectional view of a catheter holder 20 constructed in accordance with the present invention is shown. The figure, taken along line B-B¹ of FIG. 2, and showing a catheter 21, depicts holder 20 constructed with three layers. The three layers include a top layer 60, an intermediate layer 62, and a bottom layer 64. The three layers shown in the depicted embodiment combine to form the base 22 of the holder 20. The underside 31 of the extendible members 32, 34 is readily apparent. In addition, the first and second edges 27, 29 formed by the base 20 are visible at the junction between the top layer 60 and bottom layer 64.

As is apparent in FIGS. 5 and 6, the top layer 60, intermediate layer 62, and bottom layer 64 are integrally formed from the same sheet of flexible material used to make the holder 20. The sheet is folded, as discussed below, to form the holder 20. In FIG. 5, the top layer 60 and bottom layer 64 are shown connected at the edges 27 and 29. While it is not apparent from FIG. 5, intermediate layer 62 and to layer 60 are also connected to one another. This connection is best shown in FIG. 6, which is taken along line C-C¹ of FIG. 2. The layers 60, 62, 64 are preferably secured to one another by adhesive. The adhered layers provide greater rigidity than non-adhered layers.

As depicted in the embodiment shown in FIG. 6, the channel 50 is formed in the base 22 at the junctions 68, 70 where the top layer 60 folds to form the intermediate layer 62. Note that the bottom 51 of the channel 50 is formed by the bottom layer 64 of the base 22.

Figure 7:
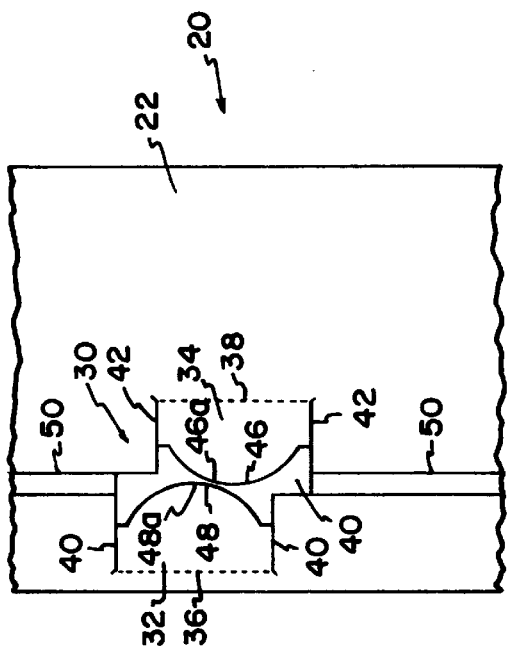
FIG. 7 is a fragmentary top plan view of a catheter holder constructed in accordance with a second embodiment of the present invention, the holder including a retainer having offset extendible members.

Referring now to FIG. 7, an additional embodiment of a retainer 30 constructed in accordance with the present invention is depicted. The retainer 30 includes two extendible members 32, 34 that flex at pivot lines 36, 38. In addition, each extendible member 36, 38 includes at least one cut line 40 or 42. The channel 50 extends on both sides of the retainer 30. In the depicted embodiment, the extendible members are positioned slightly off-center from one another. The centers 46a, 48a of each leading edge 46, 48 are also offset from each other. The distance between the centers 46a, 48a, which represents the distance by which the extendible members are offset from each other, may be varied depending upon the desired properties of the holder 20. In certain embodiments, the distance between centers 46a, 48a is between 0.1 inch and 1.0 inch. In preferred embodiments, the distance between the centers 46a and 48a is approximately 0.25 to 0.5 inch. In certain embodiments, the leading edges 46, 48 of the extendible members 32, 34 extend past the middle of the channel 50, and in some embodiments the leading edges 46, 48 extend to entirely across the channel 50. An opening 44 exposes the bottom of the retainer 20 in the depicted embodiment, thereby permitting a force to be applied to the bottom of the extendible members 32, 34 to allow the placement or removal of the catheter 21. In alternative implementations, no opening is present; however, the catheter may be placed or removed by flexing along the axis formed by the channel 50.

Figure 8:
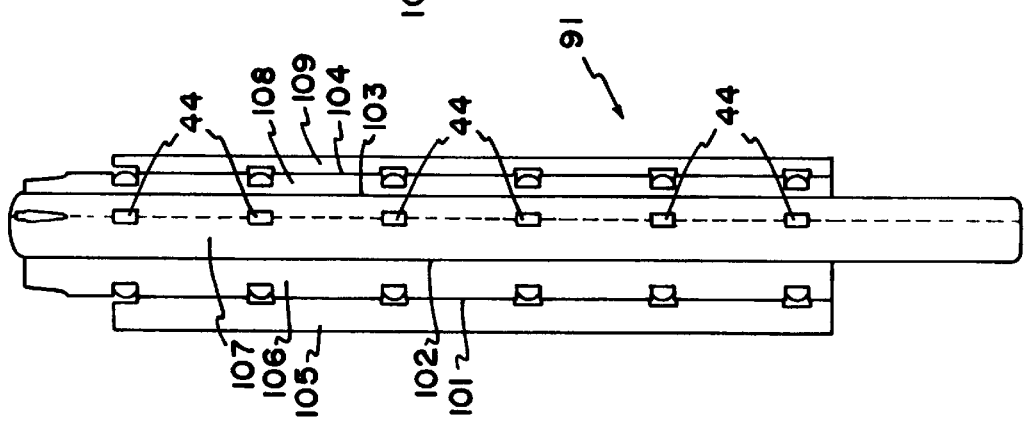
FIG. 8 is a top plan view of a card used to form a catheter holder in accordance with the present invention.

Referring now to FIG. 8, a piece of card stock 92 is depicted prior to being folded into a holder 20. Card stock 92 may be constructed of numerous materials, including paper, cardboard, and other plant-fiber products used to make packaging. Alternatively, card stock 92 may be a plastic or thermoplastic material such as polyethylene, polypropylene, and polyvinyl chloride; or a metal such as stainless steel or aluminum. Other materials that can be formed into sheets suitable for making the present catheter holder 20 may also be utilized to make the holder 20 of the present invention.

The card stock 92 is folded to form the final holder 20 shown in FIG. 1. In the embodiment shown in FIG. 8, the card stock 92 has four fold lines 101, 102, 103, 104; and five panel sections 105, 106, 107, 108, and 109. To form the holder 20, panel section 105 is folded onto panel section 106 along fold line 101. An adhesive may be applied to retain panel sections 105 and 106 together. Panel section 109 is folded along fold line 104 to partially cover panel section 108. Again, panel sections 108 and 109 may be held to one another by an adhesive. The combined panel section formed by panel sections 105 and 106 are then folded over to partially cover panel section 107. This fold occurs along line 102. The combined panel section formed by sections 108 and 109 is also folded over onto panel section 107 along fold line 103. When in this final configuration, the panel sections are preferably held to panel section 107 by an adhesive compound.

It is now readily apparent upon comparing FIG. 8 to FIG. 1 the manner in which the holder depicted in FIG. 1 is formed. Note that the corresponding parts between the card stock 92 and the holder 20 are readily identifiable. Fold line 102 of the card stock becomes the first edge 27 of the finished holder 20. Fold line 103 of the card stock 92 becomes second edge 29 of the finished holder 20. Furthermore, fold lines 101 and 102 become the boundaries of the channel 50 identified as junctions 68 and 70 in FIG. 6.

The openings 44 present in the card stock 92 are the same openings 44 depicted in the earlier figures. However, not all embodiments of the present invention include said openings 44.

Figure 9:
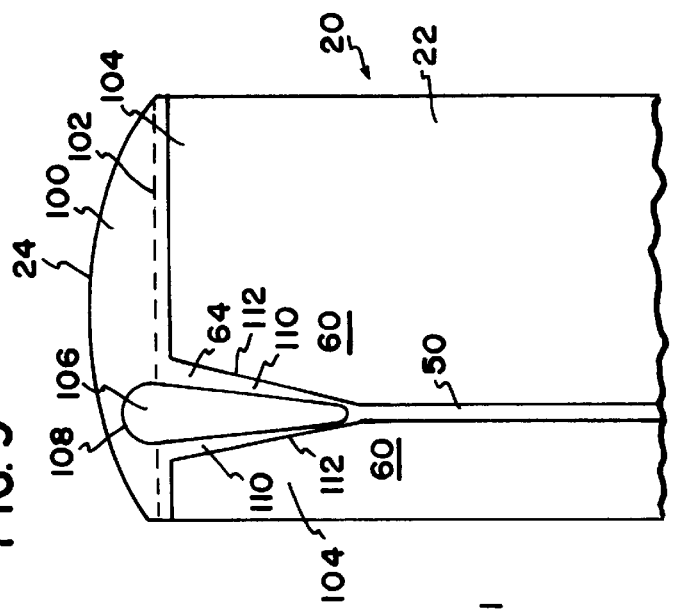
FIG. 9 is a top plan view of an end of a catheter holder constructed in accordance with the present invention for retaining the head of a catheter.

Referring now to FIG. 9, a specific embodiment for the head end 24 of the catheter holder 20 is shown. The head end 24 includes a retainer flap 100 joined to the rest of the holder 20 at retainer fold 102. In certain embodiments, retainer flap 100 is integrally formed with the base 22. In specific embodiments, the retainer flap 100 is constructed of the same panel as the bottom layer 64 of the base 22.

A catheter-receiving opening 106 is positioned such that it extends into the retainer flap 100 and the base 22. The top layer 60 of the base 22 overlies the bottom layer 64 of the base. However, in the depicted embodiment, the top layer 60 is offset from the bottom layer 64 in the vicinity of the opening 106. The exposed offset portion 110 of the bottom layer 106 is present. This offset portion 110 assists in guiding the head of the catheter 21 into the opening 106, as well as providing a resistance to the lateral sliding of the catheter head by creating a slight lip 112 on either side of the opening 106.

The retainer flap 100 extends over the top of a catheter head, and applies a downward force that retains the catheter head within the opening 106. The downward force is applied along the interior crescent edge 108 forming the portion of the opening 106 within the retainer flap 100. The upward force is applied to the catheter head by the exposed offset portions 110 of base 22. The inherent flexibility of the card stock used to form the flap 100 provides a force flexing the flap 100 downward so as to retain the catheter head.

Referring now to FIG. 10, a top plan view of an embodiment of the head end 24 of the catheter holder 20 is shown. The head end includes two head-retaining flaps 120, 122 configured to hold a catheter head in place. The flaps 120, 122 have pivot lines 121, 123 that permit the flaps 120, 122 to move up and down so as to retain the catheter head. The flaps 120, 122 may be opened by flexing the base 22 along the channel 50 at the same time as the base is flexed to open retainers 30. While the embodiment shown depicts the flaps 120, 122 with different shapes from one another, it will be appreciated that the flaps 120, 122 may also be substantially mirror images of each other.

FIG. 11 shows an embodiment for a tail portion 28 of the holder 20. In the depicted embodiment, the catheter 21 has a curled end 21a. A formed cover 120 is positioned over the end of the catheter and provides protection and a place to retain the catheter 21 end. The cover 120 is held in place at cuts 121 along the edge of the cover 120. The cover 120 is formed of a plastic material in specific implementations.

In describing the folded layers used to constructed the holder 20, it will become apparent that the present invention permits the construction of a catheter holder having improved rigidity, while enhancing the retainers 21 and the degree to which the catheters 21 are held in place. It will also be appreciated that the multiple layers of the base 22 permit the extendible members 32, 34 of the retainers to be positioned above the channel 50. The card stock 92 used to form the base 22 is of varying thickness'. The card stock 92 is from 0.001 to 0.1 inches thick in specific embodiments. The distance from the bottom 31 of the extendible members (shown in FIG. 5) to the bottom of the channel 50 may thus be approximately a multiple of the thickness of the card stock 92.

While the embodiments shown depict a single channel and a triple layer base, it will be appreciated that two, three, or more channels may be used in one holder, and that the number of layers may be varied, and may be two, three, four, five or more in number.

While the present invention has been described with reference to several particular implementations, those skilled in the art will recognize that many changes may be made hereto without departing form the spirit and scope of the present invention.

I claim:

1. A holder for retaining a catheter, the holder comprising:

an elongate base member having a first end, a second end, a top surface, and a bottom surface;

a first retainer having at least one extendible member configured and arranged to retain a catheter;

a second retainer having at least one extendible member configured and arranged to retain a catheter; and a channel in the top surface of the elongate base member connecting the first retainer and the second retainer along a line, the channel configured to receive a catheter;

wherein the channel is at least partially formed by folding the elongate base member.

2. The holder according to claim 1, wherein each of the first and second retainers further comprise an opening in the elongate base member extending from the top surface to the bottom surface, the opening configured and arranged to provide access to the extendible member.

3. The holder according to claim 1, wherein each retainer has two extendible members, each extendible member positioned on opposed sides of the channel.

4. The holder according to claim 1, wherein the extendible members comprise portions of the top surface extending over the line formed by the channel.

5. The holder according to claim 1, wherein the number of retainers on the base are from two (2) to twenty (20).

6. The holder according to claim 1, further comprising a catheter positioned within the channel and retained by the extendible members of the retainers.

7. The holder according to claim 1, wherein the first retainer and second retainer each include two extendible members.

8. The holder according to claim 7, wherein the extendible members are positioned opposite one another.

9. The holder according to claim 7, wherein the extendible members are positioned across from one another and are partially offset.

10. The holder according to claim 1, wherein the elongate base is constructed from a cellulose based material.

11. The holder according to claim 1, wherein the channel is formed by embossing the top surface of the elongate base member.

12. The holder according to claim 1, wherein the elongate base member further comprises a first edge and a second edge, and the channel is formed by folding the base member such that the first edge and second edge are proximate one another, with the channel defining the space between the first and second edges.

13. A method of placing a catheter within the holder of claim 1, the method comprising:

providing the holder;

retaining the holder;

positioning the extendible members in an extended position;

placing the catheter within the channel;

releasing the extendible members such that they hold and retain the catheter.

* * * * *